United States Patent [19]
Whitehead

[11] Patent Number: 5,920,075
[45] Date of Patent: Jul. 6, 1999

[54] ULTRAVIOLET STERILIZATION DEVICE

[76] Inventor: Michael D. Whitehead, 18732 Edleen Dr., Tarzana, Calif. 91356

[21] Appl. No.: 08/955,227

[22] Filed: Oct. 22, 1997

[51] Int. Cl.[6] ........................................................ A61L 2/10
[52] U.S. Cl. .................................... 250/492.1; 250/504 H
[58] Field of Search ........................... 250/504 H, 504 R, 250/492.1

[56] References Cited

U.S. PATENT DOCUMENTS

| | | | |
|---|---|---|---|
| 2,215,635 | 9/1940 | Collins | 250/88 |
| 2,309,546 | 1/1943 | Shapiro | 250/51 |
| 3,136,890 | 6/1964 | Wain | 250/504 H |
| 3,970,856 | 7/1976 | Mahaffey et al. | 250/493 |
| 4,221,994 | 9/1980 | Friedman et al. | 315/224 |
| 4,229,658 | 10/1980 | Gonser | 250/504 H |
| 4,471,226 | 9/1984 | Wisnosky et al. | 250/504 H |
| 4,786,812 | 11/1988 | Humphreys | 250/455.1 |
| 4,948,215 | 8/1990 | Friedman | 350/96.1 |
| 4,952,369 | 8/1990 | Belilos | 422/24 |
| 4,981,651 | 1/1991 | Horng | 422/24 |
| 5,029,252 | 7/1991 | Ameseder | 250/455.1 |
| 5,198,678 | 3/1993 | Oppawsky | 250/455.11 |
| 5,426,308 | 6/1995 | Sudduth et al. | 250/504 H |
| 5,446,289 | 8/1995 | Shodeen et al. | 250/455.11 |

*Primary Examiner*—Jack I. Berman
*Attorney, Agent, or Firm*—Blakely, Sokoloff, Taylor & Zafman, LLP

[57] ABSTRACT

A hand-held sterilization device that emits ultraviolet radiation in a range sufficient to eradicate germs, bacteria, viruses, and other pathogens and microorganisms is disclosed. The device includes a housing containing an ultraviolet light source, a power source, and an electronic safety mechanism, wherein the electronic safety mechanism includes both a switch lock circuit and a digital lock circuit that must be actuated to close an electric circuit and actuate the device. A method of using the hand-held sterilization device is also disclosed.

17 Claims, 3 Drawing Sheets

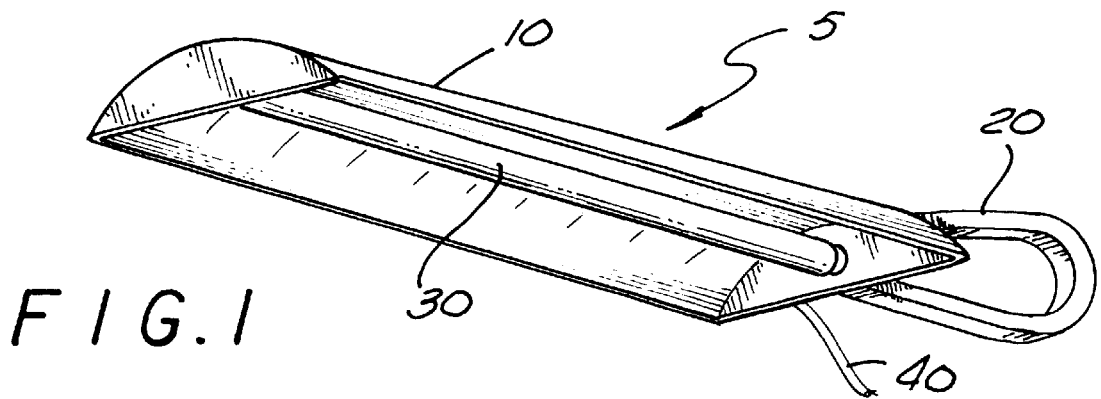
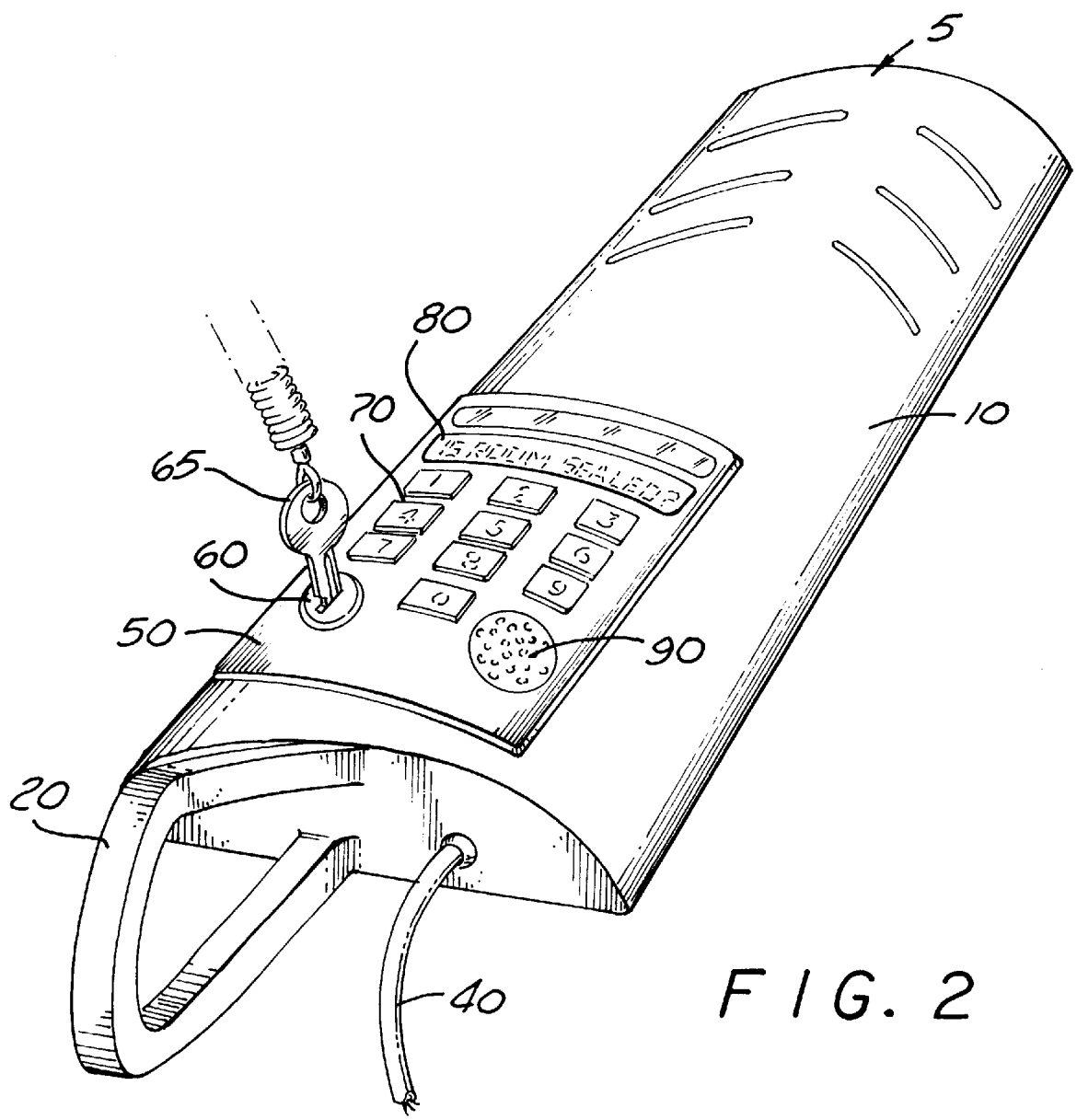

ULTRAVIOLET STERILIZATION DEVICE

BACKGROUND OF THE INVENTION

1. Field of the Invention

The invention relates generally to sterilization devices and more particularly to a hand-held ultraviolet radiation sterilization device and a method of using the same.

2. Background

UV radiation is a form of electromagnetic radiation that contains measurable wavelengths in the 4–400 nanometer range. Ultraviolet (UV) radiation is a well-known sterilization agent. The use of UV light for germicidal, bactericidal and pathogenicidal effects is well known. Suitable wavelengths for this effect is 300–200 nanometers.

Ultraviolet light is effective at eradicating germs, bacteria, viruses and other pathogens. Ultraviolet light has been used in a number of applications, including low level uses in dermatology, tanning, dental procedures, and small-scale sterilization of objects or instruments. However, to date large scale usage of ultraviolet light in hospitals or other large areas has been limited, principally because exposure to ultraviolet light at an intensity necessary for effective and efficient eradication or sterilization of pathogenic agents is very harmful to the human body. Specifically, the ultraviolet radiation required to effectively and efficiently eradicate pathogenic agents should be an intensity ranging from 2000–6000 microwatts/cm$^2$. Human contact with ultraviolet light in this range requires protective clothing, including covering the skin and eyes. UV light has been used in operating rooms, wards, and nurseries of hospitals, generally by being fixed to the walls or ceilings. The danger to humans posed by ultraviolet radiation requires these UV light sources to be shielded to prevent direct or reflected UV light from striking humans. The stationary and shielded light fixture is therefore only partially effective eradicating pathogens or of micro-organisms because there are many surfaces and hidden areas that can escape direct contact by the UV radiation.

In order for UV radiation to eradicate or kill micro-organisms, it is generally believed that the UV rays must directly strike the micro-organisms. The exposure to UV light necessary to kill bacteria (or the "kill" factor) is a product of time and intensity.

U.S. Pat. No. 2,215,635 issued to Collins (Sep. 24, 1940) discloses an adjustable ultraviolet light fixture apparatus for hospital operating rooms for treating bacteria. Collins describes maintaining the intensity of the radiation "at the highest value to which the uncovered viscera of a patient may be exposed without harmful adhesions or other undesired results ensuing." Col. 1, lines 35–38. The device includes a conventional light source and an ultraviolet radiation source attached to a positional support arm, the device fixedly mounted above an operating table to direct the light and UV radiation at the patient. The UV radiation was believed to possess bactericidal and therapeutic effects.

U.S. Pat. No. 4,952,369 issued to Belilos (Aug. 28, 1990) describes a portable, pocket-size, ultraviolet flashlight that can be used by ordinary individuals to kill germs and viruses on objects like toilet seats, flatware, and telephones. The flashlight includes a housing, an ultraviolet light source, an on/off switch, and a gravity switch that limits the activation of the ultraviolet light source to the position wherein the light source is facing downward. By limiting the activation of the UV source to when the device faces downward the device sought to reduce harm to eyes. The UV lamp utilized by Belilos can be any type of light source generating UV light in sufficient intensity to disinfect objects at relatively short distances. Col. 2, lines 6–9.

U.S. Pat. Nos. 4,786,812, 5,029,252, and 5,446,289 describe devices for sterilizing air and instruments by passing the air or instruments through the sterilization devices. U.S. Pat. No. 4,786,812 issued to Humphreys (Nov. 22, 1988) describes a device with a fan and ultraviolet light source in a housing whereby the fan draws unsterilized air into the housing and the air is sterilized and then return to its environment. U.S. Pat. No. 5,029,252 issued to Ameseder (Jul. 2, 1991) describes an apparatus with a housing containing an ultraviolet light source and the housing has openings for instrumental devices, like toothbrushes. The instrumental device is placed in the housing and sterilized by the ultraviolet light. U.S. Pat. No. 5,466,289 issued to Shodeen et al. (Aug. 29, 1995) describes a pass-through sterilization chamber where items are placed in the sterilization chamber and subjected to ultraviolet radiation.

There is a need for a UV sterilization device with sufficient intensity to kill germs, bacteria, viruses, and other pathogens and microorganisms efficiently in a large area like a hospital room. There is also a need for a hand-held device that supplies sufficient intensity to a surface or object to destroy most pathogens or microorganisms. There is further a need for a device that is capable of sterilizing rooms like, hospital operating rooms, wherein the device can reach all corners or all surfaces of the room.

SUMMARY OF THE INVENTION

The invention relates to a hand-held sterilization device that emits ultraviolet radiation in a range sufficient to destroy germs, bacteria, viruses, and other pathogens and microorganisms, by exposing surfaces and objects to unshielded, high intensity ultraviolet radiation. The device includes a housing containing an UV light source, a power source, and an electronic safety mechanism. The UV light source operates in a wavelength spectra effective to have germicidal, bactericidal, and pathogenicidal effects. The power source supplies the UV light source with sufficient intensity to effectively and efficiently destroy germs, bacteria, pathogens and microorganisms. The intensity of the UV light source is such that the radiation is unsafe to the exposed, unprotected human anatomy. An electronic safety mechanism is therefore included to regulate the power source so that only a skilled and protected operator can use the device. Further, the UV light emitted from the hand-held sterilization device is not shielded. Therefore, the light can come into direct contact with all surfaces or objects in a room. The hand-held device is simply directed throughout the room at all surfaces and objects to expose the surfaces and objects to intense UV light for a given period of time to sterilize the room.

The invention also relates to a method for sterilizing objects, the method comprising providing a hand-held sterilization device with an unshielded UV light source operating in a wavelength effective to have germicidal, bactericidal and pathogenicidal effects, supplied by a power source with sufficient intensity to be unsafe to the unprotected human anatomy but effective to have significant germicidal, bactericidal and pathogenicidal effects at significant distances from the UV light source, and passing the device over objects and surfaces of a room for a sufficient period of time.

DETAILED DESCRIPTION OF THE INVENTION

FIG. 1 is a perspective side view of the hand-held sterilization device of the invention.

FIG. 2 is a perspective top view of the hand-held sterilization device of the invention illustrating the electronic safety mechanism.

DETAILED DESCRIPTION OF THE INVENTION

Figure 3:
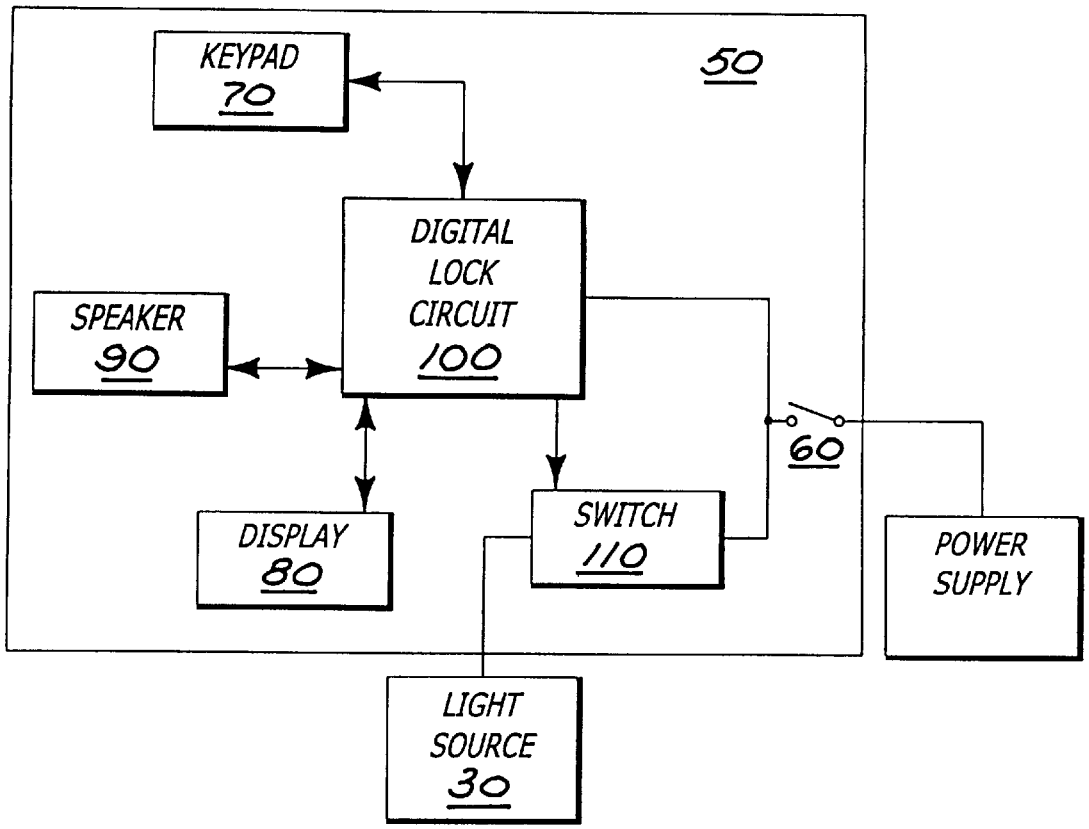
FIG. 3 is a logic diagram of the operation of the electronic safety mechanism for the hand-held sterilization device of the invention.

A hand-held sterilization device and a method for sterilizing objects utilizing a hand-held sterilization device is described herein. In the following detailed description, reference is made to specific embodiments containing particular mechanisms. These embodiments and mechanisms are to be read in an illustrative rather than a restrictive sense.

FIG. 1 illustrates the hand-held sterilization device that is the invention. The device in FIG. 1 includes a housing 10 containing an unshielded ultraviolet light source 30. The hand-held device and ultraviolet light source are powered by a power supply. In FIG. 1, the power supply is the standard power supplied to a building or hospital. In the United States, that power source is either a 110v alternating current or 220v alternating current power supply. The hand-held sterilization device 5 of FIG. 1 is coupled to the power supply through a power cord 40. The power cord 40 is of sufficient length to allow an operator of the device to maneuver throughout the room to be sterilized. It is to be understood that the power cord 40 is a conventional power cord sufficient to supply the necessary current to the hand-held sterilization device 5. It is also to be understood that coupling the device 5 to the common power source of a building is only one alternative of supplying power to the device 5. Another alternative includes a battery power supply coupled to the device 5.

The power supplied to the hand-held sterilization device 5 of FIG. 1 must be sufficient to provide the device 5 with the necessary intensity or power to have the effective germicidal, bactericidal, and pathogenicidal effects. The invention contemplates that the necessary intensity of the ultraviolet light is approximately 2000–6000 microwatts/cm$^2$. Thus, the device must be coupled to a power supply that yields the necessary measure of intensity.

The hand-held sterilization device 5 of FIG. 1 includes a handle 20 coupled to the housing. The handle 20 allows an operator to manipulate the hand-held sterilization device 5 to the necessary locations to eradicate any pathogens or microorganisms. Holding the device 5 approximately 6–18 inches over an area for approximately 1–2 seconds will be sufficient to eradicate most pathogens and microorganisms.

FIG. 2 presents a perspective top view of the hand-held sterilization device of the invention. The device 5 in FIG. 2 includes a housing 10, a handle 20 coupled to the housing, and a power cord 40 that may be connected to a power source. The device 5 in FIG. 2 further includes an electronic safety mechanism 50. The electronic safety mechanism 50 includes a switch lock 60 actuated by a key 65. The electronic safety mechanism 50 also includes a digital lock circuit made up of a numerical or alphabetical keypad 70 wherein a required numerical or alphabetical code is needed to open or turn on the power to the digital lock circuit. The digital lock circuit also includes a display 80 with prerecorded messages to prompt the user of the device as to the operation of the device 5. For example, the display pad prompts the user with queries such as, "Is the room sealed?" or "Has the room been cleared?". The electronic safety mechanism further includes a speaker 90 to provide audible signals or statements to the user regarding the use of the device 5. For example, the speaker can audiblize the query "Is the room sealed?" or "Has the room been cleared?".

FIG. 3 illustrates a logic block diagram of the electronic safety mechanism 50 of the hand-held sterilization device of the invention. To operate the device, a user must first actuate the switch lock 60 to close the circuit. Next, the user must enter the appropriate numerical or alphabetical code on the keypad 70. Entry of the proper code actuates the digital lock circuit 100 to send a control signal to actuate a switch 110 that is, for example, a relay or a transistor. The digital lock circuit 100 is, for example, a microcontroller. According to the state of the digital lock circuit 100, corresponding signals are sent to the digital display 80, that, for example, contains a light emitting diode, to visually prompt the user and the audio speaker 90 to audibly prompt the speaker of the proper use of the device. Once the proper numerical or alphabetical code is entered into the keypad 70 to actuate the digital lock circuit 100 and turn on the switch 110, power then is directed from the power supply to the light source 30 to operate the device.

Figure 4:
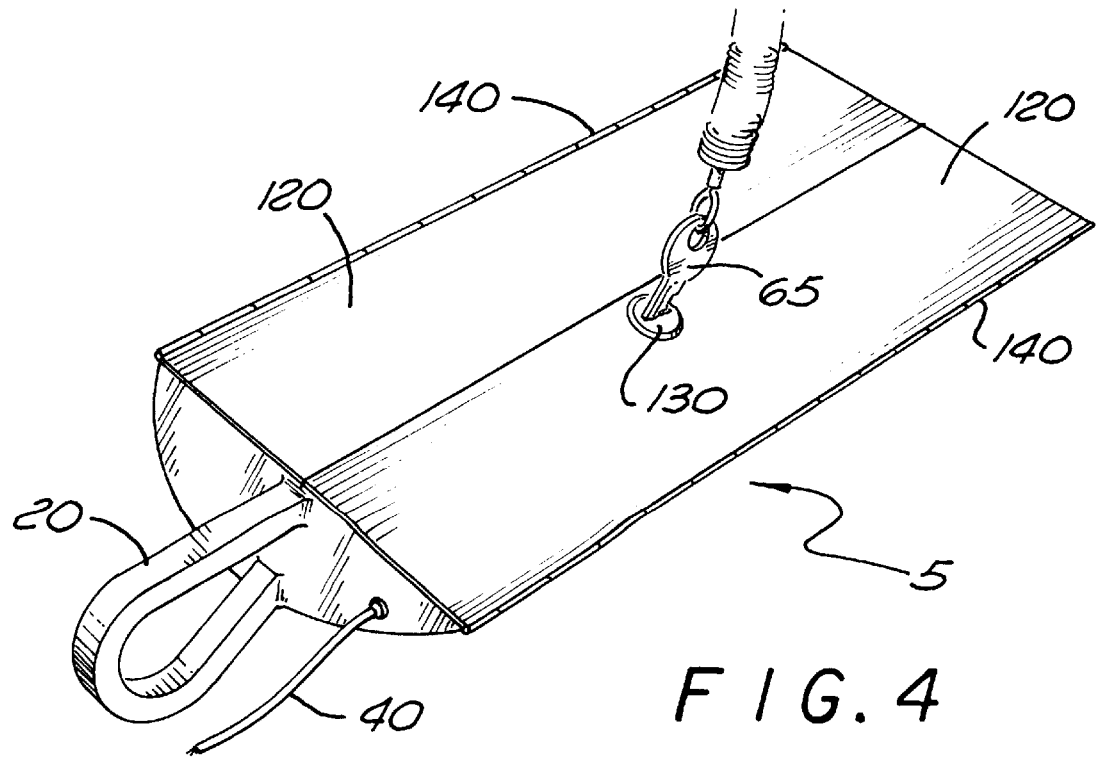
FIG. 4 is a perspective top view of the bottom side of the hand-held sterilization device of the invention.

FIG. 4 illustrates a perspective top view of the back side of the hand-held sterilization device. FIG. 4 shows the device 5 with a housing 10 and a handle 20 coupled to the housing 10. The device 5 shown in FIG. 4 includes a retractable hood 120 that is a pair of doors that open to reveal the ultraviolet light source. In FIG. 4, the doors are opened by actuating a key lock 130. The key lock is actuated by a key 65. The key 65 is the same key that actuates the switch lock on the electronic safety mechanism in FIG. 2. Thus, the invention contemplates that the same key 65 is used to expose the ultraviolet light source and to turn the light source on. The hood 120 doors are pivotably coupled to the housing by hinges 140 extending the length of the device housing 10. When the device 5 is operated and the UV radiation directed at the area to be sterilized, the hood doors are open and do not interfere with the path of the UV radiation. It should be appreciated that the hood 120 can also be electrically connected to the digital lock circuit 100 so that the hood 120 opens to reveal the light source only when the digital lock circuit 100 is actuated, for example, by an electromagnetic coupling.

Figure 5:
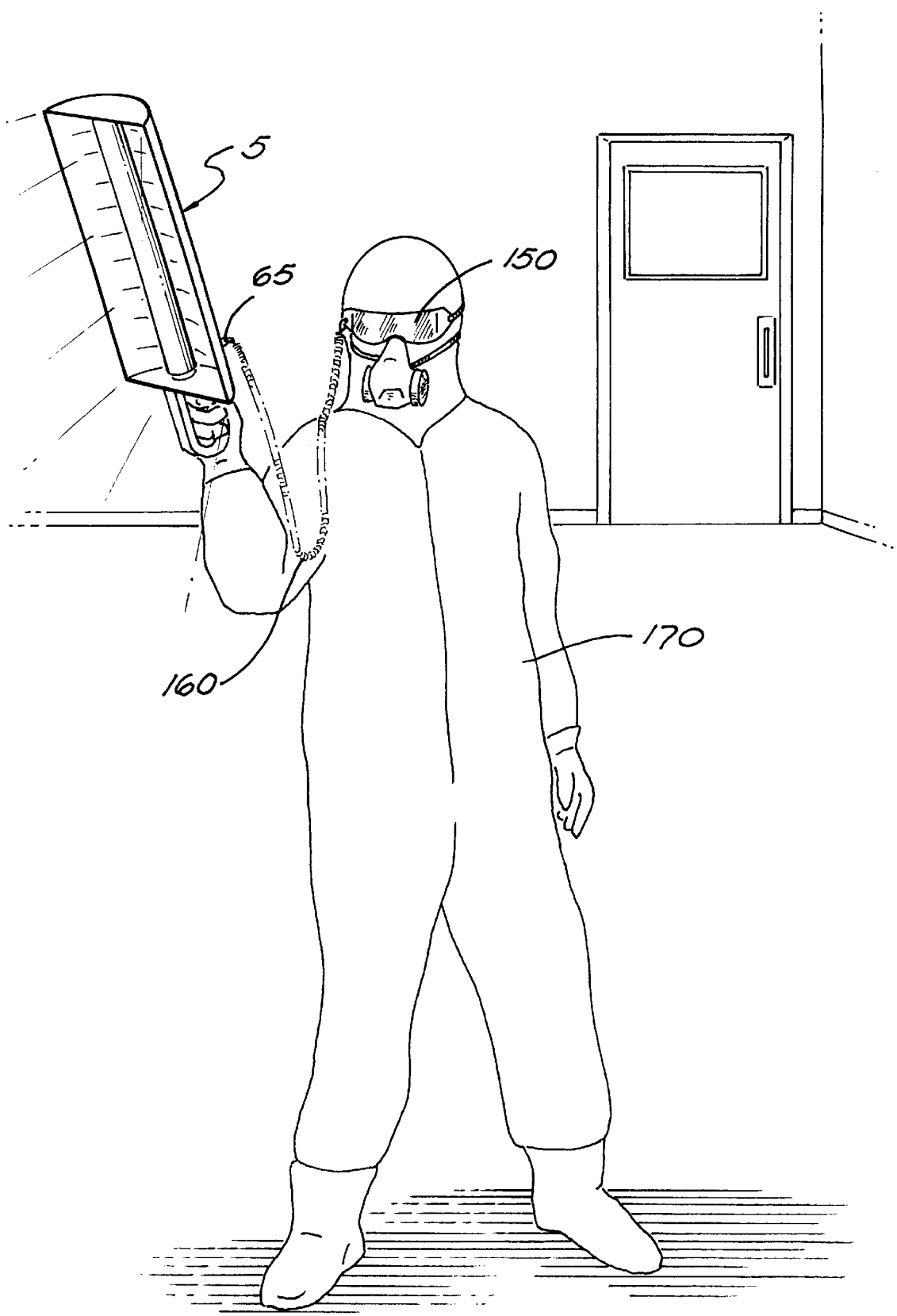
FIG. 5 is a perspective front view of the operation of the hand-held sterilization device of the invention.

FIG. 5 illustrates the use of the hand-held sterilization device 5 to sterilize a room. In FIG. 5, the operator of the device 5 wears protective clothing 170 to protect the operator from exposure to ultraviolet light. The protective clothing includes goggles 150. The goggles include a tether 160 that is attached to the key 65 that operates the electronic safely mechanism. Thus, the key 65 attached to the goggles 150 ensures that the operator will use the goggles 150 when the ultraviolet device 5 is operated.

In the preceding detailed description, the invention is described with reference to specific exemplary embodiments thereof. It will however be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A hand-held sterilization device comprising:
    a housing containing an ultra-violet light source, a power source, and an electronic safety mechanism, wherein said ultraviolet light source operates in a wavelength spectra effective to have germicidal, bactericidal, and pathogenicidal effects;

said power source operates the ultraviolet light source at an intensity emission of said ultraviolet light from said device that is unsafe to the unprotected human anatomy and effective to have germicidal, bactericidal, and pathogenicidal effects; and said electronic safety mechanism regulates said power source, wherein said electronic safety mechanism includes a switch lock attached to said housing and electrically integrated in an electric circuit with said power source, said switch lock having a first position and a second position such that said first position opens said electric circuit at said switch lock and said second position closes said circuit at said switch lock to send power to the device, and wherein said electronic safety mechanism includes a digital lock circuit coupled to said power source, such that a predetermined digital signal must be received to close said electric circuit.

2. The hand-held sterilization device of claim 1, wherein said intensity of ultraviolet light emitted from said device is approximately 2000–6000 microwatts/cm$^2$.

3. The hand-held sterilization device of claim 2, wherein said electronic safety mechanism includes one of a numerical and alphabetical keypad attached to said housing and coupled to said digital lock circuit such that a predetermined numerical or alphabetical code is entered at said keypad to send said predetermined digital signal to close said electric circuit.

4. The hand-held sterilization device of claim 3, wherein said keypad includes a visual display coupled to said digital lock circuit such that predetermined messages are broadcast on said visual display corresponding to said signals received by said digital lock circuit.

5. The hand-held sterilization device of claim 4, wherein said display screen includes a light-emitting diode.

6. The hand-held sterilization device of claim 4, wherein said keypad includes an audio speaker coupled to said digital lock circuit such that predetermined messages are broadcast on said audio speaker corresponding to said signals received by said digital lock circuit.

7. The hand-held sterilization device of claim 6, wherein said electronic safety mechanism includes a switch lock attached to said housing and electrically integrated in said electric circuit with said power source, said switch lock having a first position and a second position such that said first position opens said electric circuit at said switch lock and said second position closes said circuit at the switch lock to send power to the device.

8. The hand-held sterilization device of claim 1, wherein said housing includes a retractable hood coupled to said housing with a first position and a second position, wherein in said first position, said ultraviolet light source is completely enclosed within said hood.

9. The hand-held sterilization device of claim 8, wherein said retractable hood is electrically integrated in an electric circuit with said electronic safety mechanism such that said electronic safety mechanism actuates said retractable hood from said first position to a second position.

10. A method for sterilizing objects comprising:

providing a hand-held sterilization device that includes a housing containing an ultra-violet light source, wherein said ultraviolet light source operates in a wavelength spectra effective to have germicidal, bactericidal, and pathogenicidal effects, a power source that operates the ultraviolet light source such that the amount of said ultraviolet light emitted from said device is unsafe to the unprotected human anatomy and is effective to have germicidal, bactericidal, and pathogenicidal effects, and an electronic safety mechanism that regulates the power source, wherein said electronic safety mechanism includes a switch lock attached to said housing and electrically integrated in an electric circuit with said power source, said switch lock having a first position and a second position such that said first position opens said electric circuit at said switch lock and said second position closes said circuit at the switch lock to send power to the device, and wherein said electronic safety mechanism includes a digital lock circuit coupled to said power source, such that a predetermined digital signal must be received to close said electric circuit; and passing said hand-held sterilization device over said object for a sufficient time to have germicidal, bactericidal, and pathogenicidal effects.

11. The method of claim 10, wherein said said electronic safety mechanism of said hand-held sterilization device comprises a digital lock circuit attached to said housing coupled to said power source, and wherein said method further comprises sending a predetermined digital signal to said digital lock circuit to close said electric circuit.

12. The method of claim 11, wherein said electronic safety mechanism of said hand-held sterilization device comprises, one of a numerical and alphabetical keypad attached to said housing and electronically integrated with said digital lock circuit and said method further comprises entering a predetermined code at said keypad to send said predetermined digital signal to close said electric circuit and operate said ultraviolet light source.

13. The method of claim 12, wherein said keypad includes a visual display coupled to said digital lock circuit such that predetermined messages are broadcast on said visual display corresponding to said signals received by said digital lock circuit.

14. The method of claim 13, wherein said display screen includes a light-emitting diode.

15. The method of claim 14, wherein said keypad includes an audio speaker coupled to said digital lock circuit such that predetermined messages are broadcast on said audio speaker corresponding to said signals received by said digital lock circuit.

16. The method of claim 15 wherein said electronic safety mechanism of said hand-held sterilization device includes a light emitting diode that displays safety instructions.

17. The method of claim 16, wherein said electronic safety mechanism includes a switch lock attached to said housing and electrically integrated in an electric circuit with said power source, said switch lock having a first position and a second position such that said first position opens said electric circuit at said switch lock and said second position closes said circuit at the switch lock.

* * * * *